(12) United States Patent
Suddaby

(10) Patent No.: US 12,102,537 B2
(45) Date of Patent: Oct. 1, 2024

(54) MINIMALLY INVASIVE EXPANDABLE INTERVERTEBRAL FUSION IMPLANT

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 84 days.

(21) Appl. No.: 17/813,060

(22) Filed: Jul. 18, 2022

(65) Prior Publication Data
US 2024/0016610 A1  Jan. 18, 2024

(51) Int. Cl.
*A61F 2/44* (2006.01)
*A61F 2/30* (2006.01)

(52) U.S. Cl.
CPC .............. *A61F 2/30* (2013.01); *A61F 2/4455* (2013.01); *A61F 2002/30579* (2013.01)

(58) Field of Classification Search
CPC ........ A61F 2/441; A61F 2/442; A61F 2/4425; A61F 2/4455; A61F 2002/443
USPC ............................................. 623/17.11–17.16
See application file for complete search history.

(56) References Cited

U.S. PATENT DOCUMENTS

| | | | |
|---|---|---|---|
| 6,039,761 A * | 3/2000 | Li | A61F 2/4455 623/17.16 |
| 6,127,597 A | 10/2000 | Beyar et al. | |
| 8,025,697 B2 | 9/2011 | McClellan, III et al. | |
| 8,142,507 B2 | 3/2012 | McGuckin, Jr. | |
| 8,287,599 B2 | 10/2012 | McGuckin, Jr. | |
| 8,795,365 B2 | 8/2014 | Arcenio et al. | |
| 8,920,506 B2 | 12/2014 | McGuckin, Jr. | |
| 9,044,342 B2 | 1/2015 | Perloff et al. | |
| 9,138,327 B1 | 9/2015 | McClellan, III | |
| 9,259,324 B2 | 2/2016 | McGuckin, Jr. | |
| 9,278,008 B2 | 3/2016 | Perloff et al. | |
| 9,408,710 B2 | 8/2016 | Purcell et al. | |
| 9,655,737 B2 | 5/2017 | Perloff et al. | |
| 10,045,858 B2 | 8/2018 | Lorio et al. | |
| 10,085,844 B2 | 10/2018 | Perloff et al. | |
| 10,568,745 B2 | 2/2020 | Lorio | |
| 10,653,536 B2 | 5/2020 | Lorio et al. | |
| 10,940,016 B2 * | 3/2021 | Thommen | A61F 2/4465 |
| 10,952,868 B2 | 3/2021 | Lorio et al. | |
| 10,987,227 B2 | 4/2021 | Perloff et al. | |
| 11,234,835 B2 | 2/2022 | Jimenez et al. | |
| 2011/0066192 A1 | 3/2011 | Frasier et al. | |
| 2015/0094817 A1 * | 4/2015 | McGuckin, Jr. | A61F 2/30767 623/17.16 |
| 2015/0257894 A1 | 9/2015 | Levy et al. | |
| 2016/0143747 A1 * | 5/2016 | Agarwal | A61F 2/4455 623/17.16 |
| 2016/0199195 A1 | 7/2016 | Hauck et al. | |
| 2017/0056179 A1 | 3/2017 | Lorio | |
| 2019/0008654 A1 | 1/2019 | Thommen et al. | |

* cited by examiner

*Primary Examiner* — Eduardo C Robert
*Assistant Examiner* — Christina Negrellirodriguez
(74) *Attorney, Agent, or Firm* — Harter Secrest & Emery LLP; Michael Nicholas Vranjes

(57) ABSTRACT

An expandable intervertebral fusion implant, including a plurality of segments pivotably connected, each segment of the plurality of segments including an inferior component, and a superior component engaged with the inferior component and forming a chamber therebetween, and a first expandable bladder arranged in the chamber operatively arranged to displace the superior component with respect to the inferior component.

20 Claims, 15 Drawing Sheets

MINIMALLY INVASIVE EXPANDABLE INTERVERTEBRAL FUSION IMPLANT

FIELD

The present disclosure relates to orthopedic surgery, and more particularly to a prosthetic interbody fusion device capable of being placed within an intervertebral disc space and expanded such that interbody spinal fusion occurs.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae C1-C7 form the neck, support the head and neck, and allow nodding and shaking of the head. The thoracic vertebrae T1-T12 join with the ribs to form the rib cage. The five lumbar vertebrae L1-L5 carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal or neuro canal. The spinal cord and spinal nerves pass through the spinal canal, which protects them from injury. The spinal cord is the major column of nerve tissue that is connected to the brain and serves as an information super-highway between the brain and the body. The nerves in the spinal cord branch off to form pairs of nerve roots that travel through the small openings between the vertebrae and the intervertebral foramens.

Various medical conditions require a surgeon to repair, remove and/or replace the aforementioned discs. For example, in one surgical procedure, known as a discectomy (or diskectomy) with interbody fusion, the surgeon removes the nucleus of the disc and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 (not shown) and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, taken generally along line 6-6, but with vertebra L3 in place atop disc $D_{L3-L4}$.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. Between the vertebral bones themselves exist soft tissue structures, i.e., discs, composed of fibrous tissue and cartilage that are compressible and act as shock absorbers for sudden downward forces on the upright column. The discs allow the bones to move independently of each other, as well. The repetitive forces which act on these intervertebral discs during repetitive activities of bending, lifting, and twisting cause them to break down or degenerate over time.

Presumably, because of humans' upright posture their intervertebral discs have a high propensity to degenerate. Overt trauma or covert trauma, occurring in the course of repetitive activities, disproportionately affects the more highly mobile areas of the spine. Disruption of a disc's internal architecture leads to bulging, herniation, or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal movement.

The time-honored method of addressing the issues of neural irritation and instability resulting from severe disc damage has largely focused on removal of the damaged disc and fusing the adjacent vertebral elements together. Removal of the disc relieves the mechanical and chemical irritation of neural elements, while osseous union (i.e., bone knitting) solves the problem of stability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union. Intervertebral prosthesis in various forms has therefore been used to provide immediate stability and to protect and preserve an environment that fosters growth of the grafted bone such that a structurally significant bony fusion can occur.

Limitations of most present-day intervertebral implants are significant and revolve largely around the marked variation in the disc space height and shape that result from either biologic variability or pathologic change. For example, if a disc space is 20 mm in height, a circular implant bridging this gap requires a minimum diameter of 20 mm just to contact the end plate of the vertebral bone. Generally, end plate disruption must occur to allow a generous bony union, meaning that an additional 2-3 mm must be added on either side resulting in a final implant size of 24-26 mm. During implantation from an anterior approach (i.e., from the front of the body), excessive retraction (or pulling) is often required on the great blood vessels, which greatly enhances the risk of devastating complications such as vascular tears or thrombosis. On the other hand, during a posterior approach, large implant diameters may require excessive traction on neural elements for adequate placement, even if all posterior bony elements are removed. In some instances, an adequate implant size cannot be inserted posteriorly, particularly if there is a significant degree of distraction to obtain stability by tightening the annular ligamentous tension band. Compromising on implant size risks sub-optimal stability or a loose implant, which has a greater risk of migration within, or expulsion from, the disc space. The alternative of excessively retracting neural elements to facilitate a posterior implant application results in a neuropraxia at best and permanent neural damage at worst.

More recently, expandable polyether ether ketone (PEEK) and titanium cages have been developed which can expand in a vertical dimension and in some cases laterally as well to allow smaller incisions and less tissue dissection and retraction permitting the insertion using minimally invasive techniques. These purely mechanical devices require complex expansion and locking mechanisms which not only limit their expansile capabilities, but also because they are contained within the device, take up most of the real estate that would normally be utilized for bone graft housing in a normal open but static device. Because of the limited area for bone graft containment and housing and because long term fusion is dependent on bone growth, many expandable devices compromise bone graft surface area resulting in limited fusion of one vertebra to another or in no fusion at all, whereon the device subsides into the vertebrae through a thin endplate and ultimately serves no therapeutic purpose.

Clearly, there is a need in the art and science of spinal fusion surgery for an interbody fusion device which can be inserted using minimally invasive techniques as through an endoscopic tube or portal such that the device can be expanded within a suitably prepared disc space. There is also a need for such interbody fusion device to be capable of expansion occurring in three dimensions to allow restoration of disc space height and ligamentous tautness, while preserving a generous and protected space for bone graft and thereby fostering the best possible interbody fusion via the smallest possible insertion portal.

SUMMARY

According to aspects illustrated herein, there is provided an expandable intervertebral fusion implant, comprising a plurality of segments pivotably connected, each segment of the plurality of segments including an inferior component, and a superior component engaged with the inferior component and forming a chamber therebetween, and a first expandable bladder arranged in the chamber operatively arranged to displace the superior component with respect to the inferior component.

In some embodiments, the plurality of segments form a first end and a second end, the second end being connected to the first end. In some embodiments, the plurality of segments are operatively arranged to form a polygon. In some embodiments, the plurality of segments form a radially inward facing surface, the expandable bladder being arranged radially outward of the radially inward facing surface. In some embodiments, the expandable intervertebral fusion implant further comprises a second expandable bladder engaged with the radially inward facing surface. In some embodiments, the second expandable bladder is operatively arranged to laterally expand the expandable intervertebral fusion implant. In some embodiments, the first expandable bladder is operatively arranged to vertically expand the expandable intervertebral fusion implant.

In some embodiments, the inferior component comprises a first plate arranged to engage a first vertebra and a first protrusion extending from the first plate, and the superior component comprises a second plate arranged to engage a second vertebra and a second protrusion extending from the second plate, the second protrusion engaged with the first protrusion. In some embodiments, the first plate, the second plate, and at least one of the first protrusion and the second protrusion form the chamber. In some embodiments, at least one of the first plate and the second plate comprises a through-hole. In some embodiments, the superior component engages the inferior component via a plurality of teeth. In some embodiments, the plurality of segments are pivotably connected via one or more pins. In some embodiments, the expandable intervertebral fusion implant further comprises a mesh tube connected to at least one segment of the plurality of segments and including an internal cavity, the first expandable bladder arranged in the mesh tube.

According to aspects illustrated herein, there is provided an expandable intervertebral fusion implant, comprising a plurality of segments pivotably connected, each segment of the plurality of segments including an inferior component comprising a first plate and a first protrusion extending from the first plate, a superior component comprising a second plate and a second protrusion extending from the second plate, the second protrusion engaged with the first protrusion, and a chamber formed between the inferior component and the superior component, and a first expandable bladder arranged in the chamber, wherein the superior component is displaceable with respect to the inferior component in a first direction, and the plurality of segments are displaceable in a second direction, different than the first direction.

In some embodiments, the expandable intervertebral fusion implant further comprises a radially inward facing surface formed by at least one of the first protrusion of the plurality of segments and the second protrusion of the plurality of segments. In some embodiments, the expandable intervertebral fusion implant further comprises a second expandable bladder removably engaged with the radially inward facing surface. In some embodiments, the first expandable bladder is arranged radially outward of the first protrusion and the second protrusion. In some embodiments, the plurality of segments are capable of forming a linear array of segments, and a polygon. In some embodiments, the first expandable bladder is operatively arranged to displace the superior component with respect to the inferior component.

According to aspects illustrated herein, there is provided an expandable intervertebral fusion implant, comprising a plurality of segments pivotably connected, each segment of the plurality of segments including an inferior component including a first plate and a first plurality of protrusions extending from the first plate, a superior component including a second plate and a second plurality of protrusions extending from the second plate, the second plurality of protrusions engaged with the first plurality of protrusions, and a chamber formed between the first plate and the second plate, and an expandable bladder arranged in the chamber and operatively arranged to displace the superior component with respect to the inferior component.

According to aspects illustrated herein, there is provided a method of deploying an expandable intervertebral fusion implant including a plurality of pivotably connected segments, the method comprising arranging the plurality of pivotably connected segments in a substantially linear array, expanding the plurality of pivotably connected segments in a first direction using a first bladder, expanding the plurality of pivotably connected segments in a second direction, different than the first direction, using a second bladder.

In some embodiments, the method further comprises, prior to the step of expanding the plurality of pivotably connected segments in the first direction using the first bladder, inserting the plurality of pivotably connected segments into an intervertebral disc space.

According to aspects illustrated herein, there is provided an interbody spinal fusion device comprising a rigid or flexible plastic or titanium outer wall and an inner inflatable bladder capable of being filled with a hardenable material such that a plastic or metal fusion device can be inserted into a suitably prepared interbody space through a small opening, expanded to a customized size determined by individual anatomy, and fixated in situ such that a customized implant can be inserted through minimally invasive techniques.

The present disclosure relates to orthopedic surgery and more particularly to a prosthetic interbody fusion device that can be configured within an interbody space by inflating it with a hardenable material such that interbody spinal fusion can be carried out utilizing minimally invasive surgical techniques, and all the preferred surface/bone interface characteristics are retained while providing a generous cavity for bone graft housing.

According to aspects illustrated herein, there is provided a minimally invasive inflatable fusion device comprising traditional metal and/or plastic polymers capable of being expanded in three dimensions all while preserving the maximal space for housing bone graft material and minimizing device subsidence by positioning the expansile portion of the device adjacent to the cortical ring of the vertebra where the strongest and most dense bone is found.

In some embodiments, the minimally invasive inflatable fusion device comprises a flexible outer wall including plastic, PEEK, or metal (e.g., titanium) mesh, and/or hinged modular solid expandable devices, the outer wall forming an inner chamber containing an expandable bladder. When inflated, the expandable bladder expands the mesh or modular outer wall component until the mesh or module is fully expanded or until disc height or ligamentous tautness is properly restored.

Optimal expansion of the device can be determined either through radiographic parameters (i.e., height restoration, anteroposterior (AP) or lateral dimensions, etc.), pressure measurements obtained when inflating the device, or a combination of both. Volumetric measurements may also be utilized.

Once the ideal size, shape, and footprint of the device has been achieved, the pressure is held for a predetermined amount of time (e.g., approximately five minutes) until the injected material hardens into a concrete device, the center portion of which is then filled with products to facilitate bone fusion, for example, autograft, allograft, and xenograft bone tissue, alloplast (hydroxyapatite, tricalcium phosphate (TCP), bioglass, etc.), bone morphogenic protein (BMP), etc.

To ensure that the device is always ideally positioned adjacent to the cortical ring, a second inflatable balloon or bladder is inflated within the center of the device to push it out to the disc perimeter and hold it there while waiting for the hardenable material to solidify (i.e., facilitate lateral expansion). The second central balloon is filled with contrast or saline so that it can be deflated and removed and the space it occupied filled with bone graft material. It should be appreciated that the device can be expanded laterally first and the expanded vertically, or vice versa.

According to aspects illustrated herein, there is provided a minimally invasive intervertebral disc replacement implant, deployed using one or more of the following steps. In a first step, the deflated implant is inserted into a disc space between two vertebrae. The implant comprises a plurality of links or segments hingedly or pivotably connected such that the implant can be easily folded in half or in any geometric shape. In some embodiments, the plurality of segments may look similar to a bicycle chain. This shape makes it easier to be arranged in the intervertebral disc space through a minimally invasive opening. Thus, the implant comprises a hingedly or pivotably connected plurality of segments. In a second step, the implant is expanded laterally using a first balloon or expansion mechanism. The first balloon is arranged on the radially inward facing surface of the plurality of segments. As the first balloon is inflated, the implant takes the lateral shape of the removed disc and/or adjacent vertebrae. The first balloon can be inflated with a removable fluid, for example, saline with a contrast in it to be viewed using videography, fluoroscopy, or some other form of viewing assistance. In a third step, the implant is expanded vertically using a second balloon. The second balloon is arranged within the plurality of segments. In some embodiments, each segment of the plurality of segments may comprise a piston like arrangement including a superior component slidably engaged with an inferior component and creating a channel therebetween, the second balloon residing in the channel. As the second balloon is inflated, the implant expands to the desired disc height. The second balloon can be inflated with a hardenable material or a removable material. In a fourth step, once the hardenable material hardens, the fluid within the first balloon is removed and the first balloon is removed from the implant, leaving an empty space in the middle of the expanded implant. In a fifth step, the empty space is filled with bone material (e.g., autograft bone or artificial bone). The purpose of the present disclosure is to be able to replace a disc using a minimally invasive procedure, wherein all of the components described herein can fit through a small tube, for example.

In some embodiments, the device comprises at least one of a segmented mesh and a hinged segmented module. In some embodiments, the device comprises a hinged module section on the back or sides and a mesh component anteriorly to achieve greater degree of radiolucency or to allow greater expansion anteriorly to aid in finer control of lordosis in the final endoprosthesis configuration. The device comprises an inflatable balloon or bladder contained within the mesh or module. In some embodiments, the balloon is elastomeric and the linked mesh or module ultimately stops expansion of the elastomeric balloon; although, in some embodiments non-elastomeric balloons or bladders could also achieve the same degree of expansion, albeit with an intrinsic positive stop of their own.

In some embodiments, the endoprosthesis is inserted into a prepared disc from any access trajectory known in the art (i.e., posterior, lateral, anterior, or oblique), through a small portal. Once positioned across the disc space, the center balloon is inflated pushing the mesh or modules out peripherally such that they are positioned circumferentially beneath the cortical rim of the vertebra. This positioning balloon can be elastomeric, non-elastomeric, or a combination thereof. It is filled with radiopaque contrast media or saline as desired, but not with hardenable material since it will be evacuated and withdrawn once the endoprosthesis has set. Once the endoprosthesis is positioned circumferentially beneath the cortical ring, it is inflated/expanded vertically to ensure that the disc height restoration is optimal. The center balloon keeps it in position while inflation of the endoprosthesis is carried out. The endoprosthesis can be inflated vertically with saline to confirm positioning, after which the saline is removed and a hardenable material is injected and held in position until firmly solidified. Once this occurs, the center positioning balloon is deflated and removed. The space occupied by the positioning balloon is then filled with bone products to facilitate bony fusion and long-term spinal stability. It should be appreciated that by using titanium, in either the mesh or module embodiment, surface characteristics or porosity can be altered to favor bony ingrowth into the prosthesis; although other materials can be used.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

Figure 1:
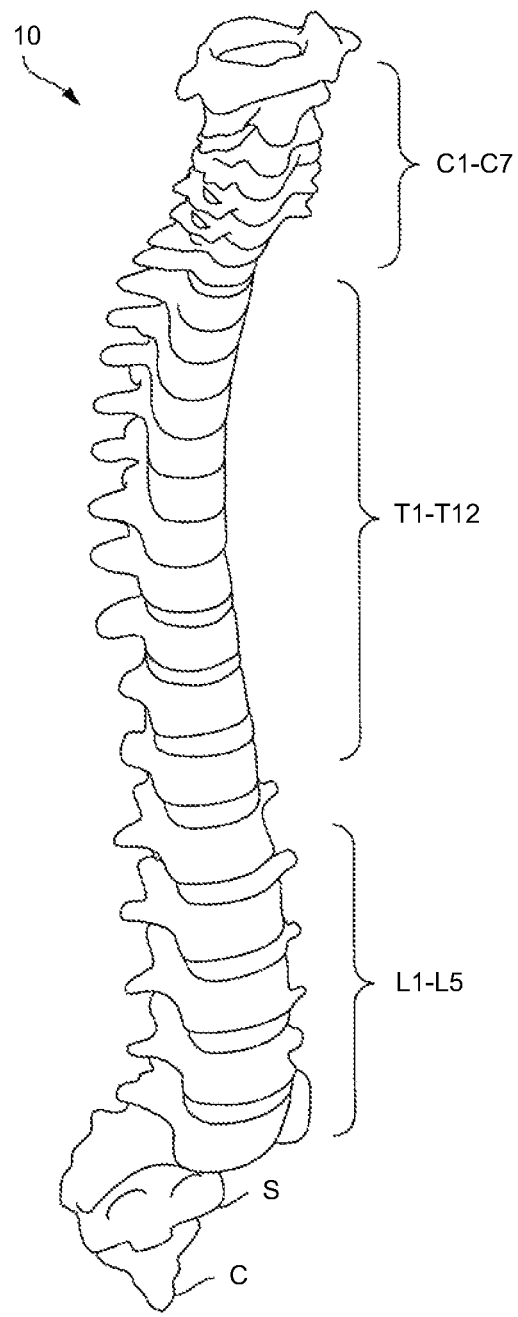
FIG. 1 is an anterior perspective view of a spinal column.
Figure 2:
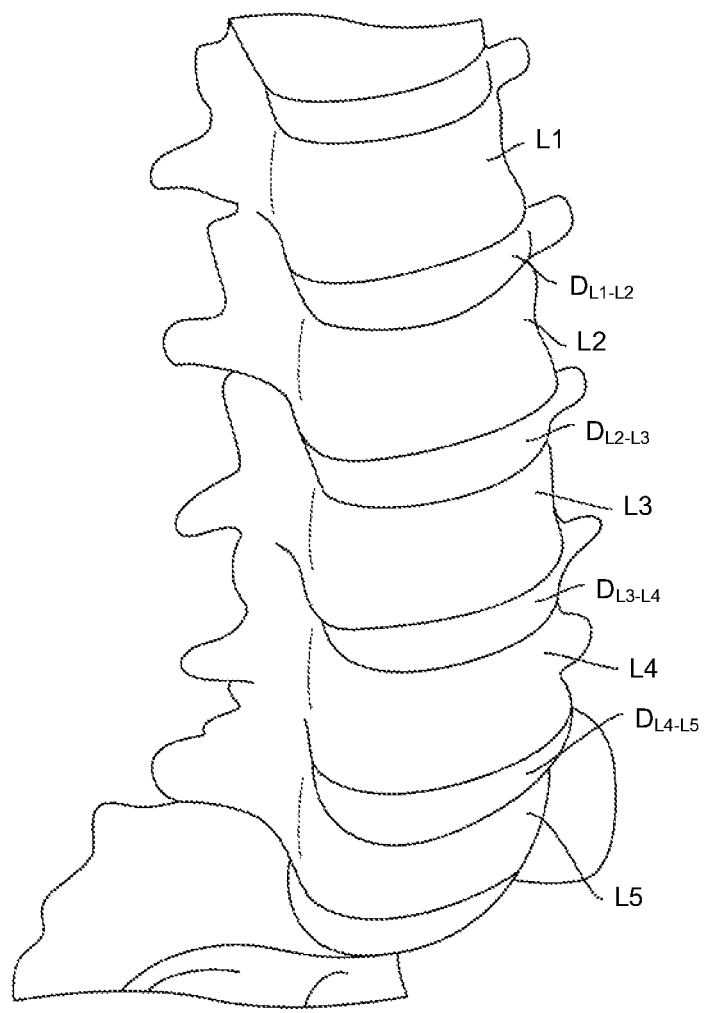
FIG. 2 is an anterior perspective view of the lumbar section of the spinal column shown in FIG. 1.
Figure 3:
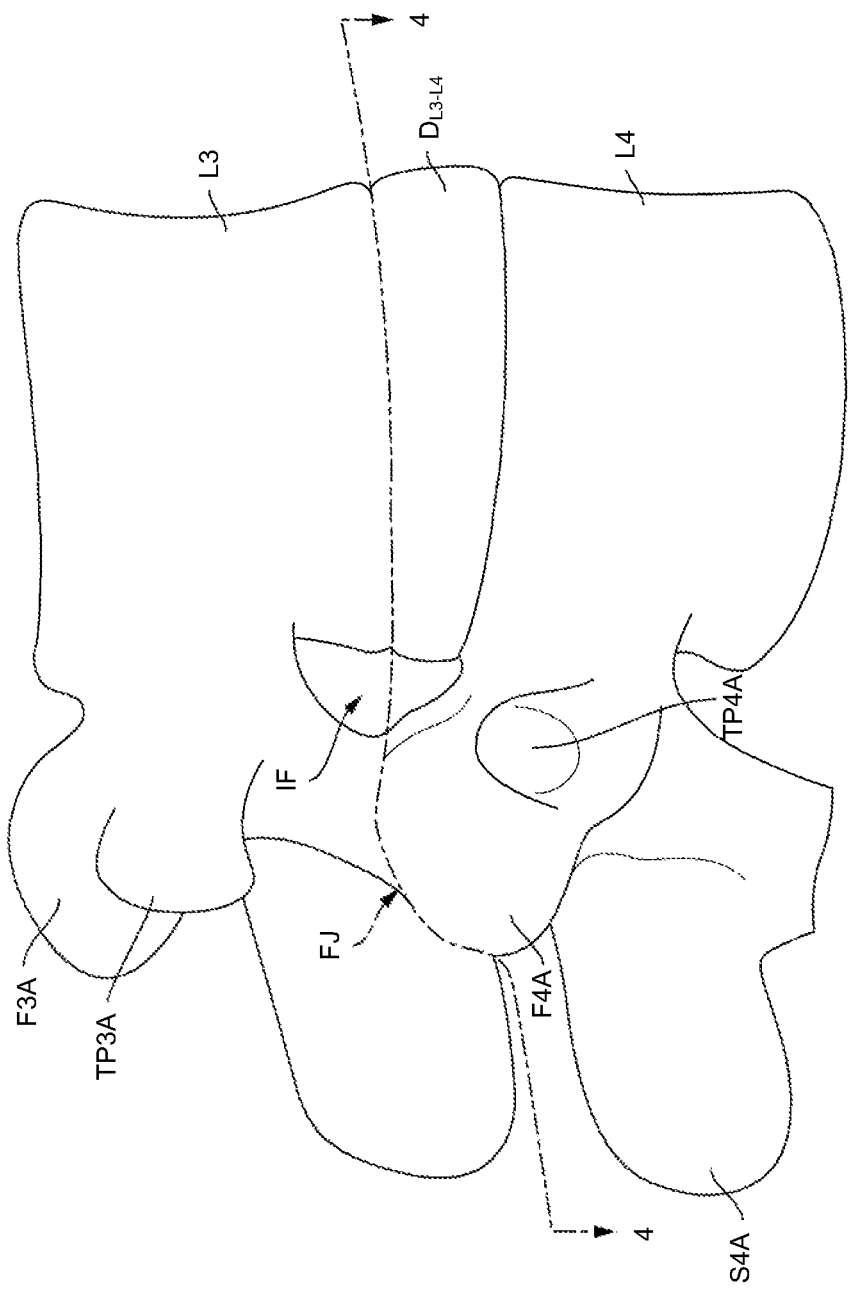
FIG. 3 is a lateral perspective view of two vertebrae, a disc, and related spinal anatomy.
Figure 4:
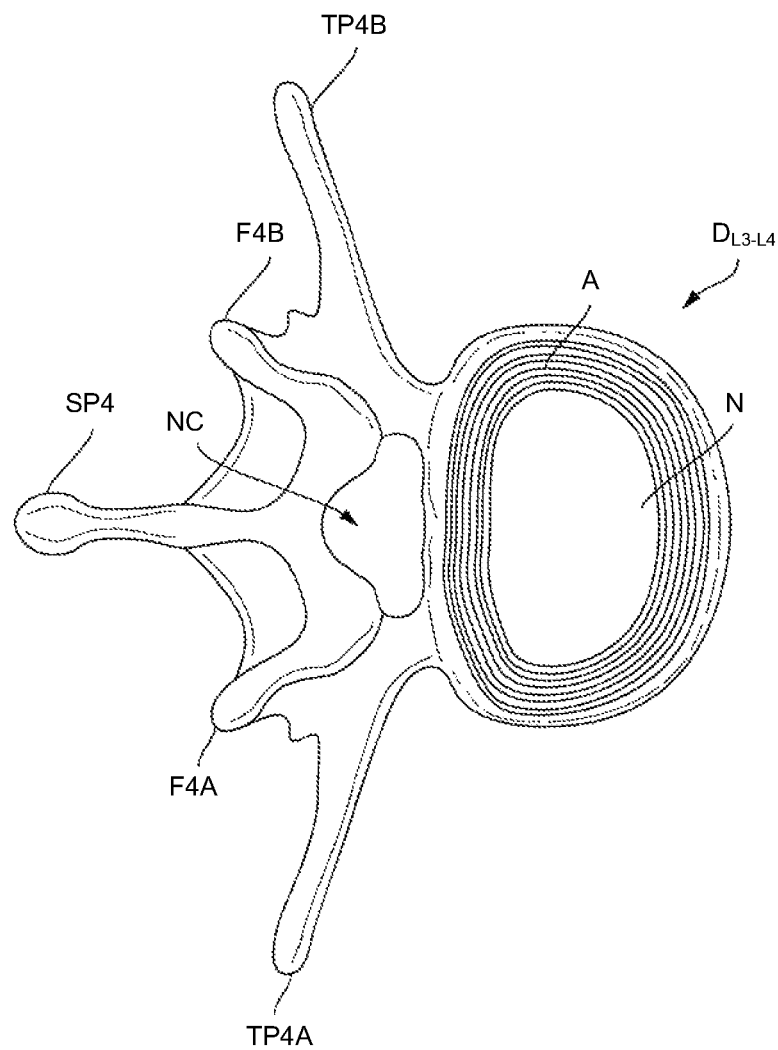
FIG. 4 is a top view of a section of the spinal column, taken generally along line 4-4 in FIG. 3.
Figure 5:
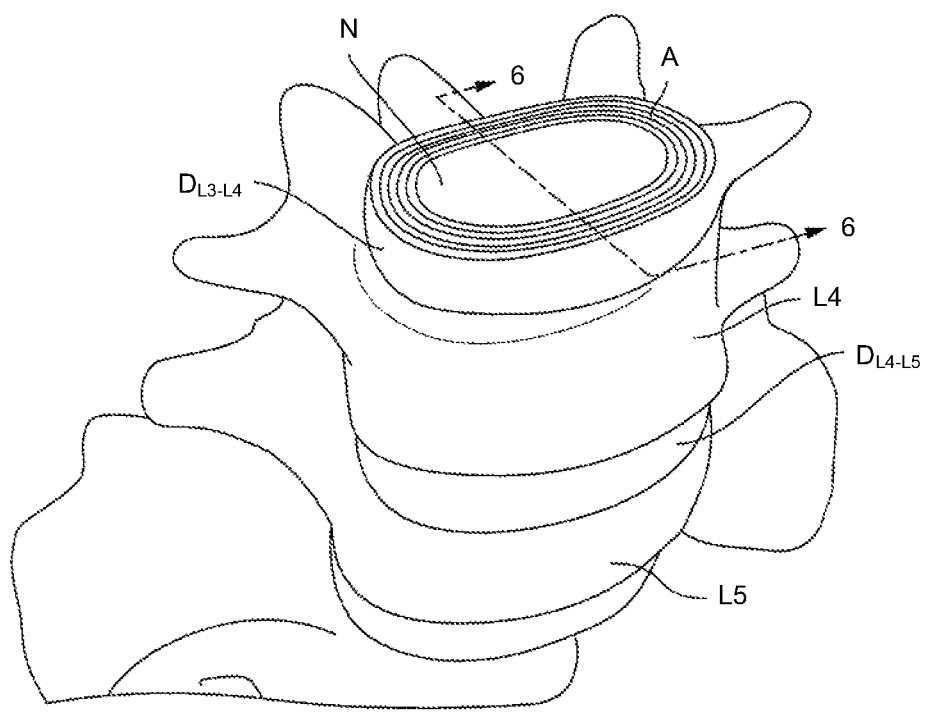
FIG. 5 is an enlarged anterior perspective view of the spinal column shown in FIG. 2, except with the top vertebra and all other structure above the top vertebra removed.
Figure 6:
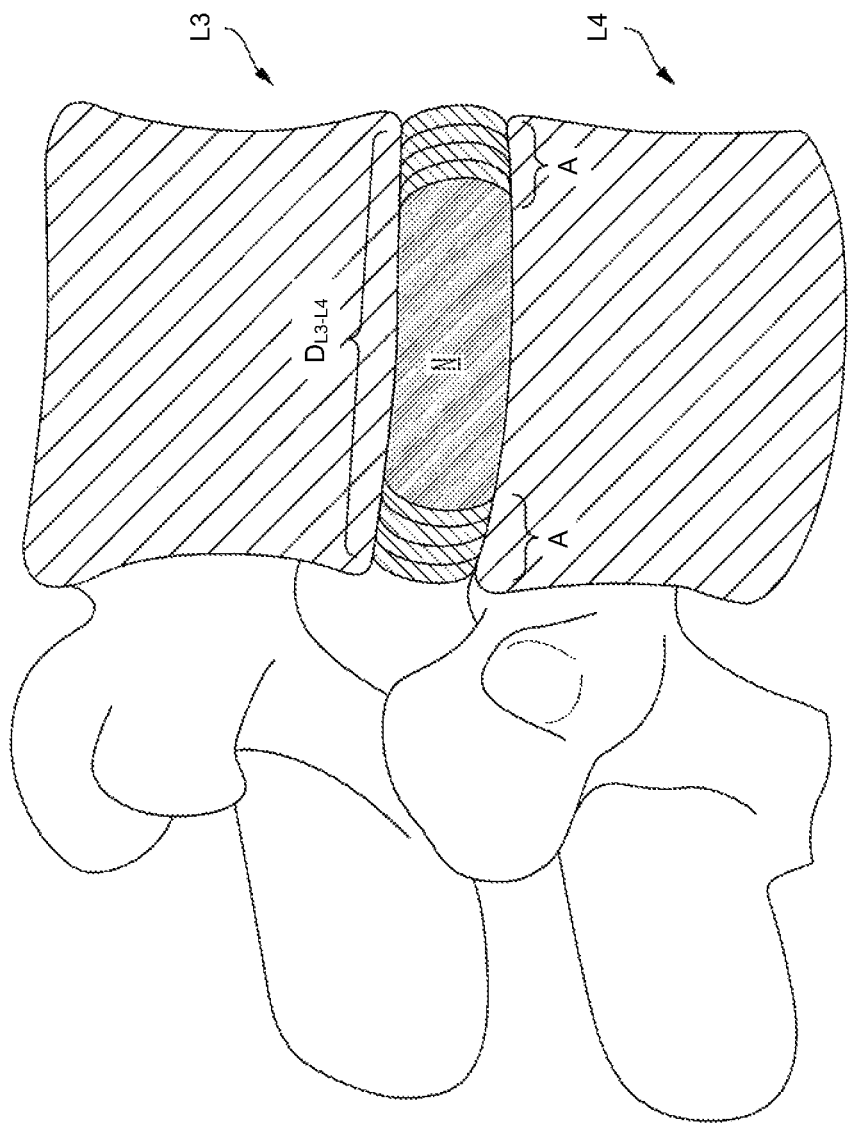
FIG. 6 is a partial cross-sectional view of the top and bottom vertebrae and disc, taken generally along line 6-6 in FIG. 5.

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be understood that use of "or" in the present application is with respect to a "non-exclusive" arrangement, unless stated otherwise. For example, when saying that "item x is A or B," it is understood that this can mean one of the following: (1) item x is only one or the other of A and B; (2) item x is both A and B. Alternately stated, the word "or" is not used to define an "exclusive or" arrangement. For example, an "exclusive or" arrangement for the statement "item x is A or B" would require that x can be only one of A and B. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Moreover, as used herein, the phrases "comprises at least one of" and "comprising at least one of" in combination with a system or element is intended to mean that the system or element includes one or more of the elements listed after the phrase. For example, a device comprising at least one of: a first element; a second element; and, a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" is used herein.

Adverting now to the figures, and as described previously, FIGS. 1-6 depict various parts and sections of spinal anatomy.

Figure 7A:
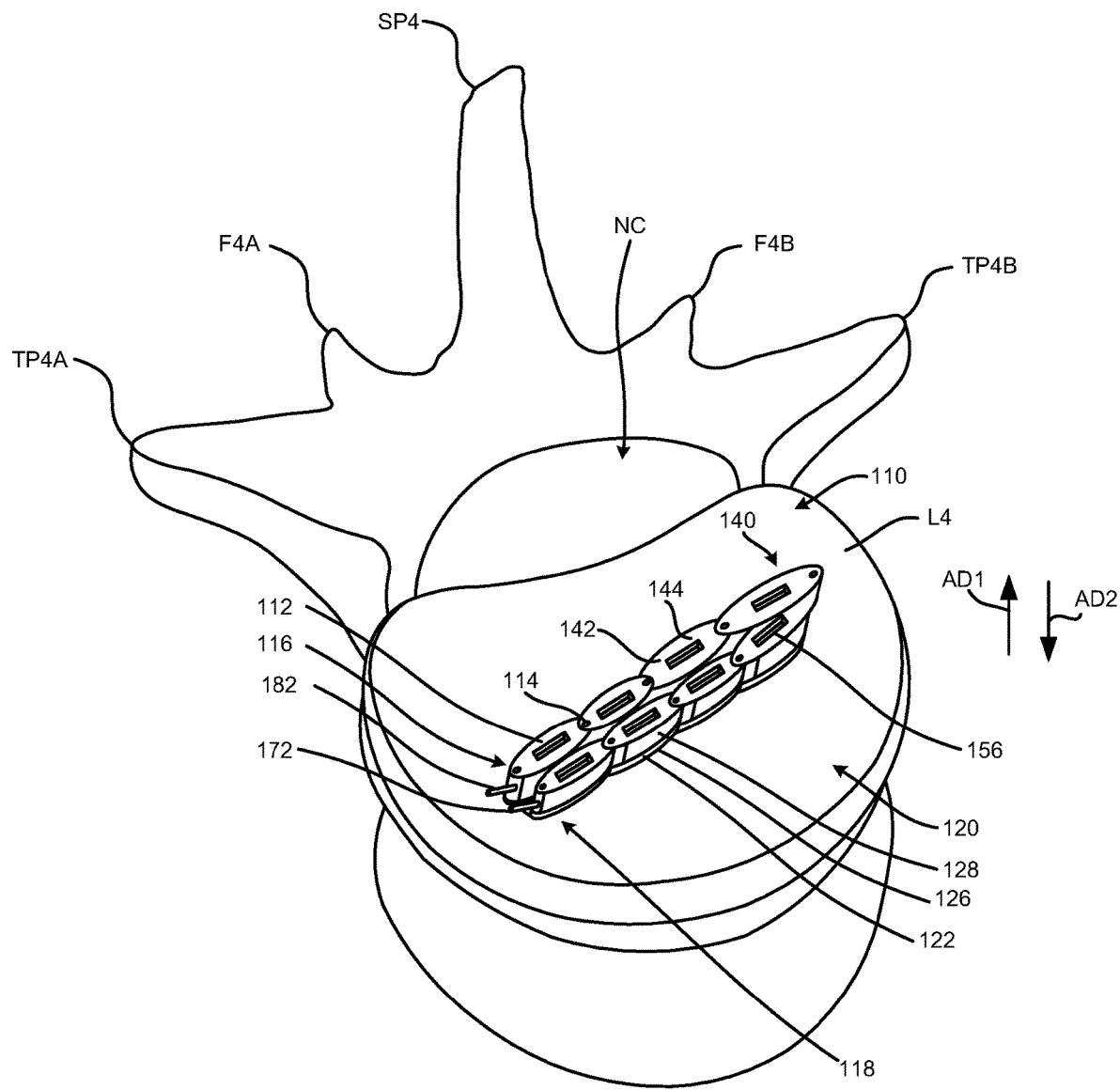
FIG. 7A is a perspective view of an expandable intervertebral implant engaged with a vertebra, in a collapsed state.
Figure 7B:
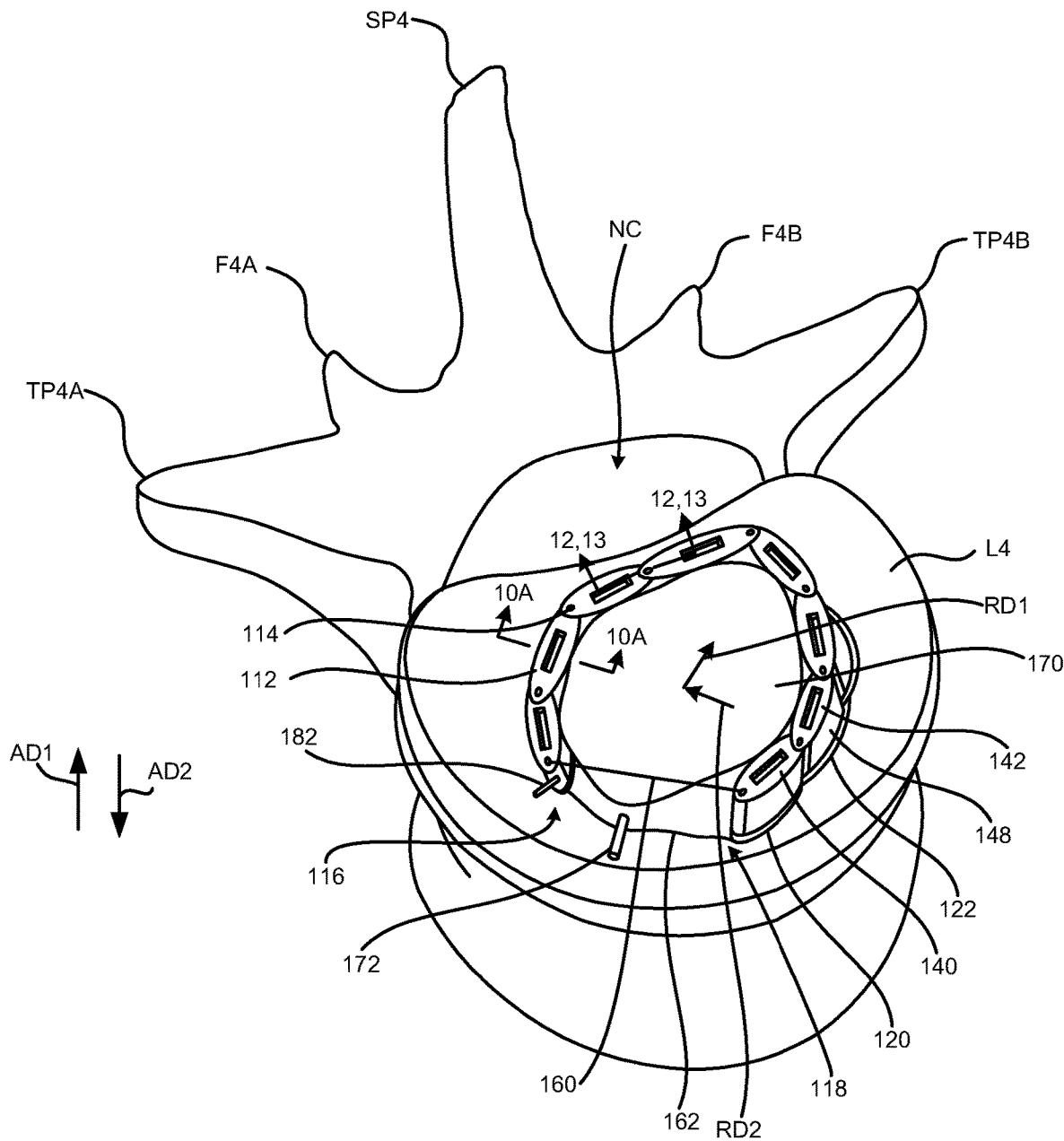
FIG. 7B is a perspective view of an expandable intervertebral implant engaged with a vertebra, in a partially expanded state.
Figure 7C:
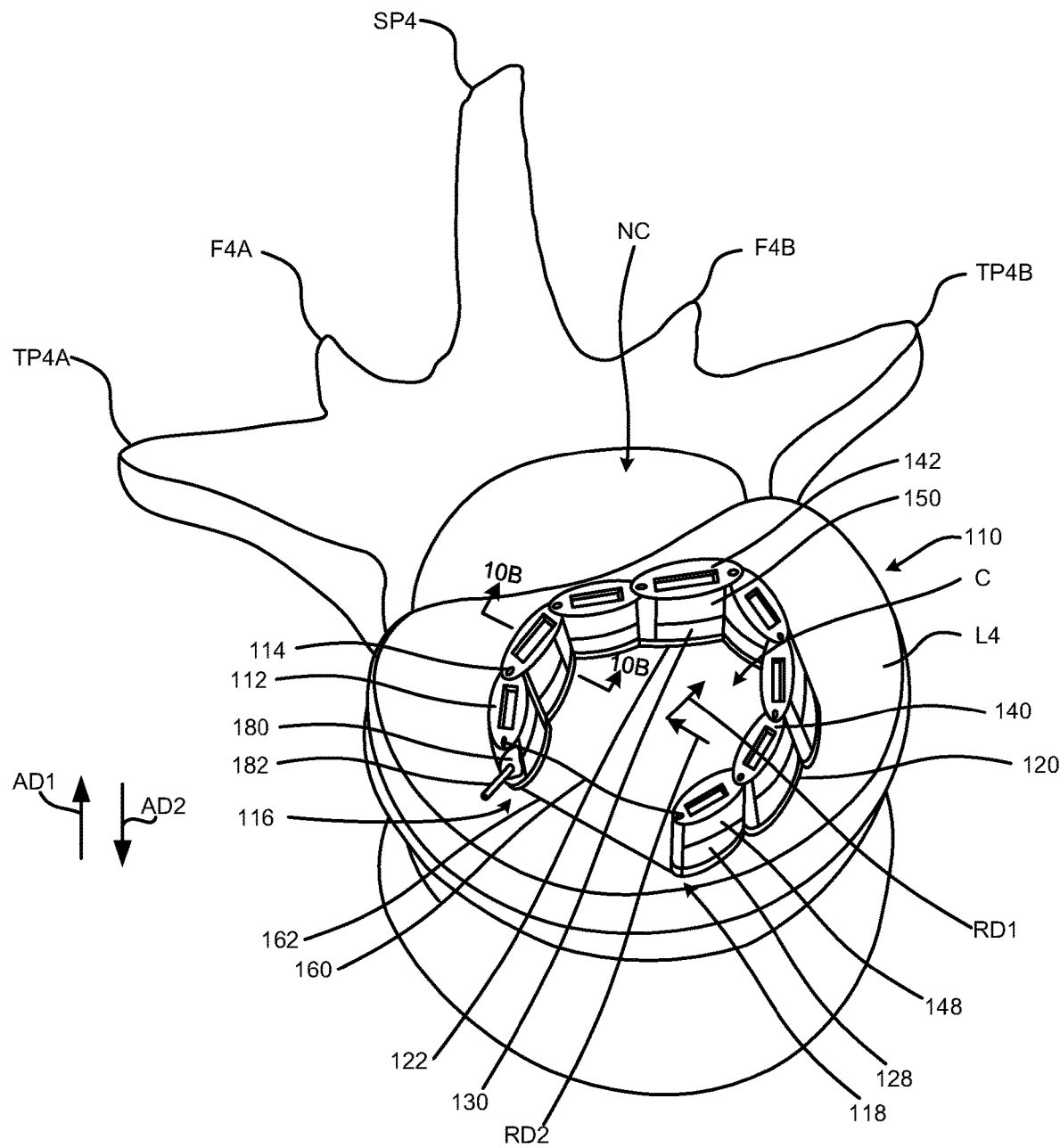
FIG. 7C is a perspective view of an expandable intervertebral implant engaged with a vertebra, in a fully expanded state.
Figure 8:
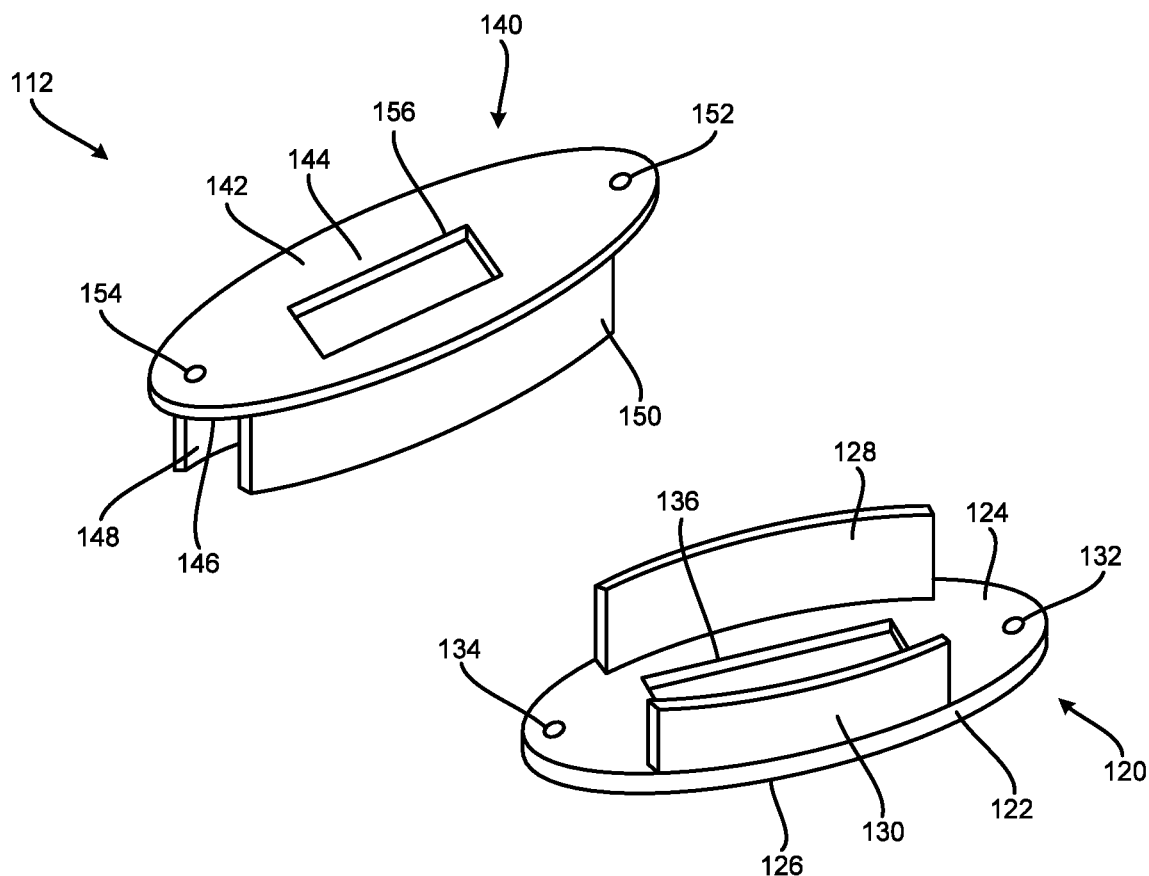
FIG. 8 is a perspective exploded view of a segment of the expandable intervertebral implant shown in FIG. 7A.

FIG. 7A is a perspective view of expandable intervertebral implant 110 engaged vertebra L4, in a collapsed state. FIG. 7B is a perspective view of expandable intervertebral implant 110 engaged with vertebra L4, in a partially expanded state. FIG. 7C is a perspective view of expandable intervertebral implant 110 engaged with vertebra L4, in a fully expanded state. FIG. 8 is a perspective exploded view of segment 112 of expandable intervertebral implant 110.

Expandable intervertebral implant 110 comprises a plurality of segments or modules 112 pivotably connected via connectors or pivots 114. Implant 110 comprises end 116 and end 118. In some embodiments, and as shown, the segments forming end 116 and end 118 are connected via one or more lines or connectors or tethers, for example, line 160 and line 162. In some embodiments, line 160 and/or line 162 are elastic (i.e., capable of elastic deformation). In some embodiments, line 160 and/or line 162 are non-elastic (i.e., not capable of elastic deformation). In some embodiments, the segments forming end 116 and end 118 are directly connected to each other via pivot 114.

Each of segments 112 comprises inferior component 120 and superior component 140. Superior component 140 is displaceable in axial direction AD1 and AD2 with respect to inferior component 120. Inferior component 120 comprises plate 122 including top or inner surface 124, bottom or outer surface 126, and at least one protrusion or wall extending from top surface 124, for example, protrusion 128 and protrusion 130. In some embodiments, plate 122 comprises through-bore 132 arranged at a first end and through-bore 134 arranged at a second end. Through-bores 132 and 134 are used to pivotably connect inferior component 120 to adjacent segments 112. In some embodiments, plate 122 further comprises through-hole 136 operatively arranged to allow bone material to engage adjacent vertebrae from within implant 110, as will be described in greater detail below.

Protrusion 128 is operatively arranged to engage superior component 140, for example, protrusion 148, and forms at least a portion of a radially outward facing surface of implant 110. Protrusion 130 is operatively arranged to engage superior component 140, for example protrusion 150, and forms at least a portion of a radially inward facing surface of implant 110. Top surface 124, protrusion 128, and protrusion 130 form an inner chamber within which bladder or balloon 180 is arranged.

In some embodiments, and as shown, protrusion 128 does not extend the entire length of plate 122, but rather is arranged between and spaced apart from the ends of plate 122. Similarly, in some embodiments, protrusion 130 does not extend the entire length of plate 122, but rather is arranged between and spaced apart from the ends of plate 122. The arrangement of protrusions 128 and 130 essentially creates two tab portions of plate 122 at its two ends, these tab portions being used to engage and connect with adjacent segments 112 while still allowing pivotable movement between segments 112. In some embodiments, protrusion 128 is aligned with or arranged proximate to an outer edge of plate 122. In some embodiments, protrusion 130 is aligned with or arranged proximate to an outer edge of plate 122.

Superior component 140 comprises plate 142 including top or outer surface 144, bottom or inner surface 146, and at least one protrusion or wall extending from bottom surface 146, for example, protrusion 148 and protrusion 150. In some embodiments, plate 142 comprises through-bore 152 arranged at a first end and through-bore 154 arranged at a second end. Through-bores 152 and 154 are used to pivotably connect superior component 140 to adjacent segments 112. In some embodiments, plate 142 further comprises through-hole 156 operatively arranged to allow bone material to engage adjacent vertebrae from within implant 110, as will be described in greater detail below.

Protrusion 148 is operatively arranged to engage inferior component 120, for example, protrusion 128, and forms at least a portion of a radially outward facing surface of implant 110. In some embodiments, protrusions 128 and 148 are slidingly engaged. Protrusion 150 is operatively arranged to engage inferior component 120, for example protrusion 130, and forms at least a portion of a radially inward facing surface of implant 110. In some embodiments, protrusions 130 and 150 are slidingly engaged. Bottom surface 148, protrusion 148, and protrusion 150 form an inner chamber within which bladder 180 is arranged. The sliding engagement of protrusions 128, 130, 148, and 150 maintain alignment and orientation of superior component 140 with respect to inferior component 120. For example, the sliding engagement of protrusions 128, 130, 148, and 150 generally form a piston-like connection between superior component 140 and inferior component 120. In some embodiments, at least one of protrusions 128, 130, 148, and 150 is a curvilinear plate.

In some embodiments, and as shown, protrusion 148 does not extend the entire length of plate 142, but rather is arranged between and spaced apart from the ends of plate 142. Similarly, in some embodiments, protrusion 150 does not extend the entire length of plate 142, but rather is arranged between and spaced apart from the ends of plate 142. The arrangement of protrusions 148 and 150 essentially creates two tab portions of plate 142 at its two ends, these tab portions being used to engage and connect with adjacent segments 112 while still allowing pivotable movement between segments 112. In some embodiments, protrusion 148 is aligned with or arranged proximate to an outer edge of plate 142. In some embodiments, protrusion 150 is aligned with or arranged proximate to an outer edge of plate 142. In some embodiments, through-bore 152 is aligned with through-bore 132 and/or through-bore 154 is aligned with through-bore 134. In some embodiments, through-bore 152 is not aligned with through-bore 132 and/or through-bore 154 is not aligned with through-bore 134.

Figure 9:
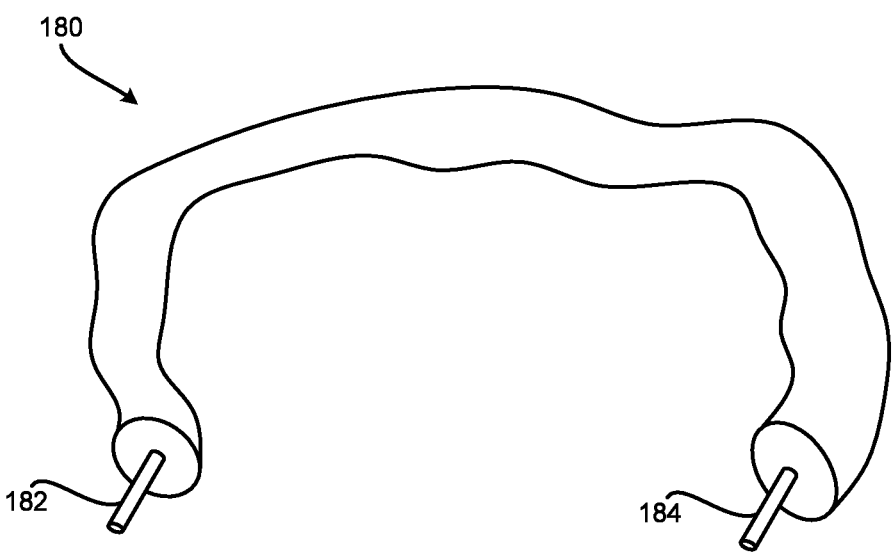
FIG. 9 is a perspective view of the bladder shown in FIG. 7A.
Figure 10A:
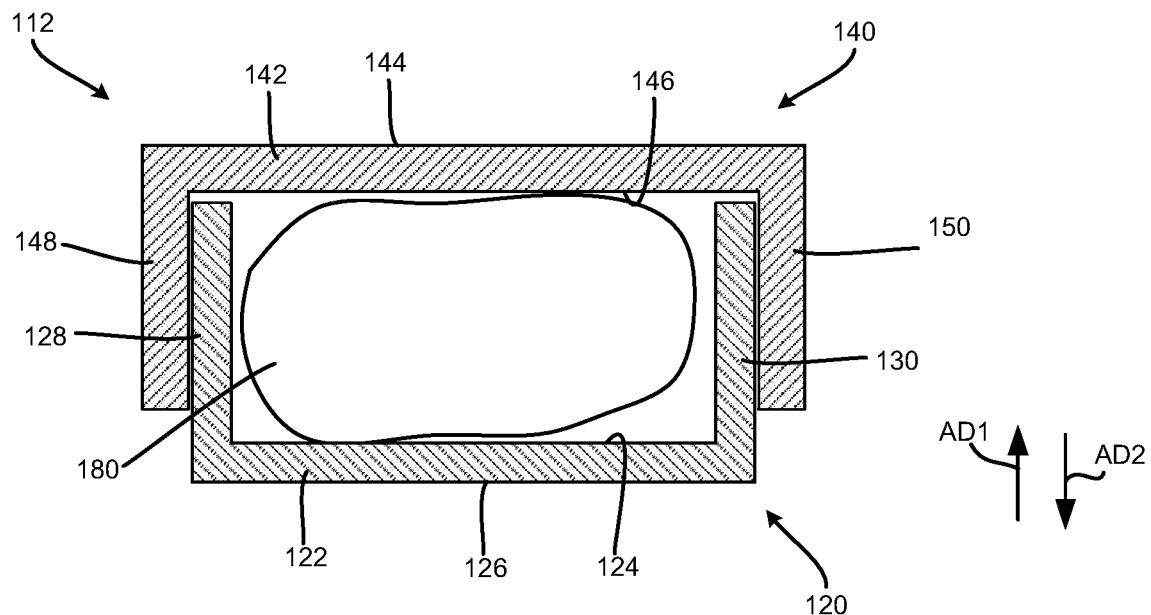
FIG. 10A is a cross-sectional view of the expandable intervertebral implant taken generally along line 10A-10A in FIG. 7B.
Figure 10B:
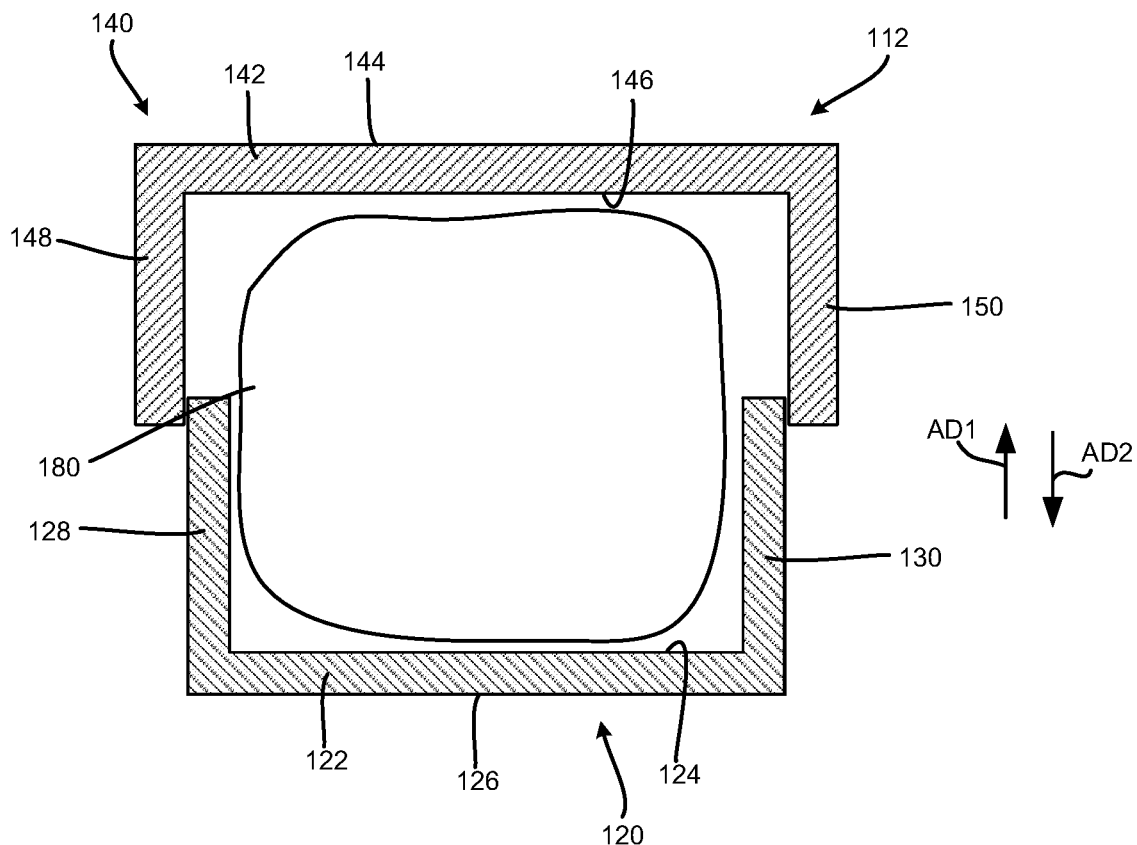
FIG. 10B is a cross-sectional view of the expandable intervertebral implant taken generally along line 10B-10B in FIG. 7C.

FIG. 9 is a perspective view of bladder 180. FIG. 10A is a cross-sectional view of expandable intervertebral implant 110 taken generally along line 10A-10A in FIG. 7B. Figure is a cross-sectional view of expandable intervertebral implant 110 taken generally along line in FIG. 7C. Bladder 180 is arranged in the inner chamber of the plurality of segments 112 formed by inferior components 120 and superior components 140. Bladder 180 comprises a first end arranged proximate end 116 and a second end arranged proximate end 118. Bladder 180 is operatively arranged to be filled with a material and expanded, for example, via port 182. In some embodiments, bladder 180 further comprises a second port 184. Specifically, bladder 180 engages surface 124 and surface 146. In some embodiments, bladder 180 further engages at least one of protrusions 128, 130, 148, and 150. FIG. 10A shows segment 112 in a vertically collapsed state. In a collapsed state, protrusions 128 and 130 may engage or be arranged proximate to surface 146. As bladder 180 is filled with a material (e.g., saline, hardenable material, etc.), it expands and engages at least surfaces 124 and 146, thereby displacing superior component 140 with respect to inferior component 120. Implant 110 is expanded vertically until the desired disc height is achieved. FIG. 10B shows segment 112 in a vertically expanded state.

In some embodiments, bladder 180 is first filled with saline or another easily removable material to confirm positioning of implant 110 proximate the cortical ring of adjacent vertebrae. Once the position of implant 110 is confirmed, the saline is removed from bladder 180, after which a hardenable material is injected into bladder 180 via port 182 and/or port 184. The hardenable material is sealed within bladder 180 at a predetermined pressure until it solidifies, at which point the pressure may be released. In some embodiments, after the hardenable material solidifies, ports 182 and/or 184 may be removed. The two-port embodiment shown in FIG. 9 may help distribute the internal forces more evenly throughout bladder 180.

Figure 11A:
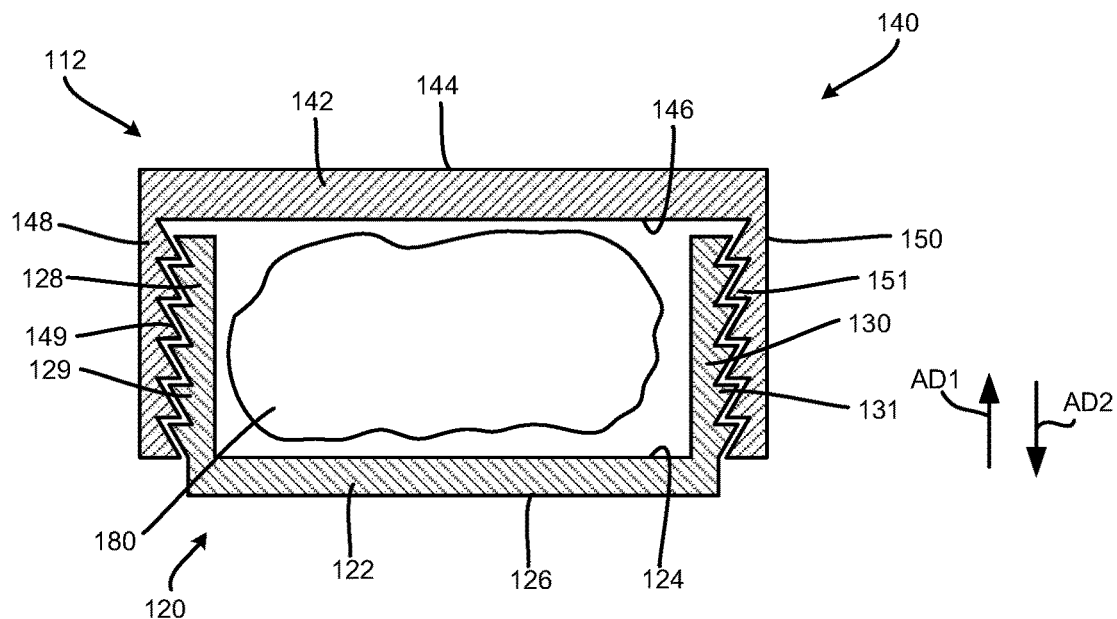
FIG. 11A is a cross-sectional view of the expandable intervertebral implant taken generally along line 10A-10A in FIG. 7B.
Figure 11B:
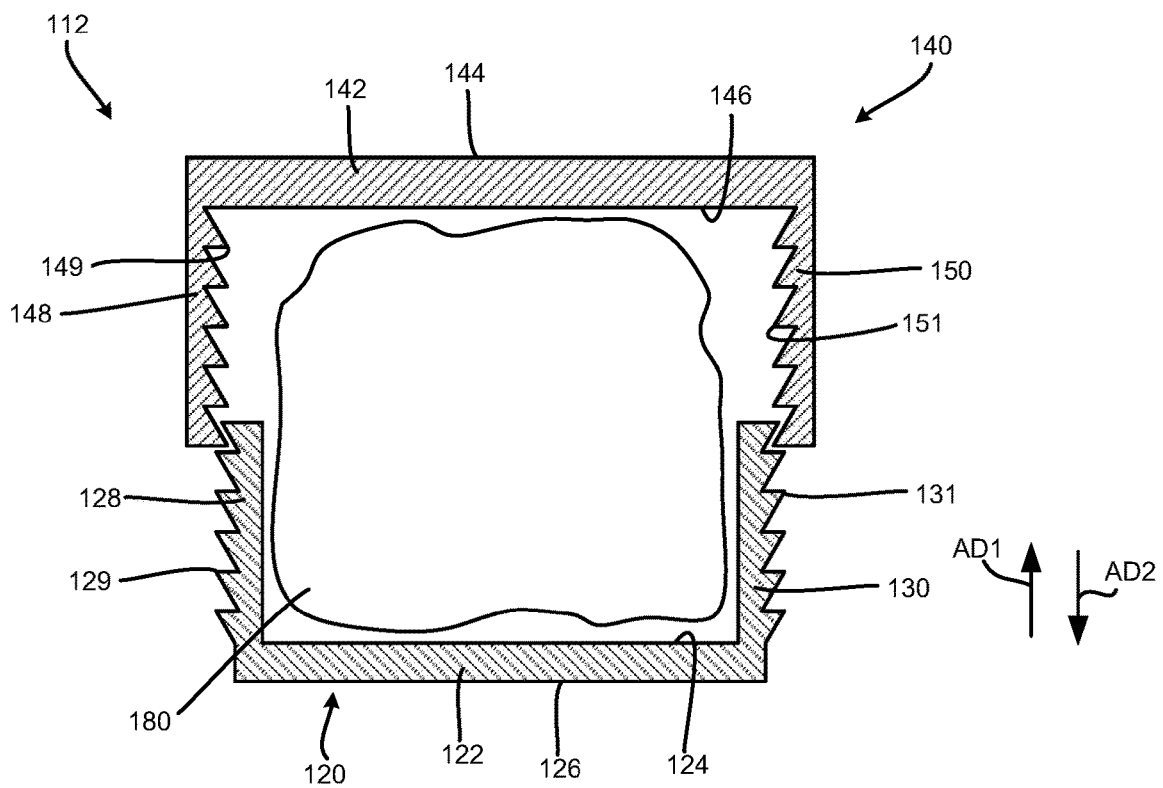
FIG. 11B is a cross-sectional view of the expandable intervertebral implant taken generally along line 10B-10B in FIG. 7C.

In some embodiments, segments 112 may ultimately be filled with a bone material, for example, autograft, allograft, and xenograft bone tissue, alloplast (hydroxyapatite, TCP, bioglass, etc., BMP, STC, etc. An example of such embodiments is shown in FIGS. 11A-B, wherein superior component 140 is engaged with inferior component 120 via a plurality of teeth. For example, protrusion 128 comprises at least one tooth 129 and protrusions 130 comprises at least one tooth 131. Protrusion 148 comprises teeth 149 operatively arranged to engage at least one tooth 129 and protrusion 150 comprises teeth 151 operatively arranged to engage at least one tooth 131. The engagement of teeth allows displacement of superior component 140 in axial direction AD1 but prevents displacement of superior component 140 in axial direction AD2 with respect to inferior component 120.

In such embodiments, bladder 180 is expanded with a saline or other material that can be easily removed therefrom until the desired height of segments 112 is achieved, as shown in FIG. 11B. The saline is removed from bladder 180, but the engagement of teeth between superior component 140 and inferior component 120 maintain the desired height (i.e., prevent segments 112 from collapsing). Subsequently, bladder 180 can be removed from implant 110 and bone material can be injected into implant 110 using any suitable technique. Specifically, each of segments 112 can be filled with bone material, which can engage and fuse with adjacent vertebrae via through-holes 136 and 156.

Figure 12:
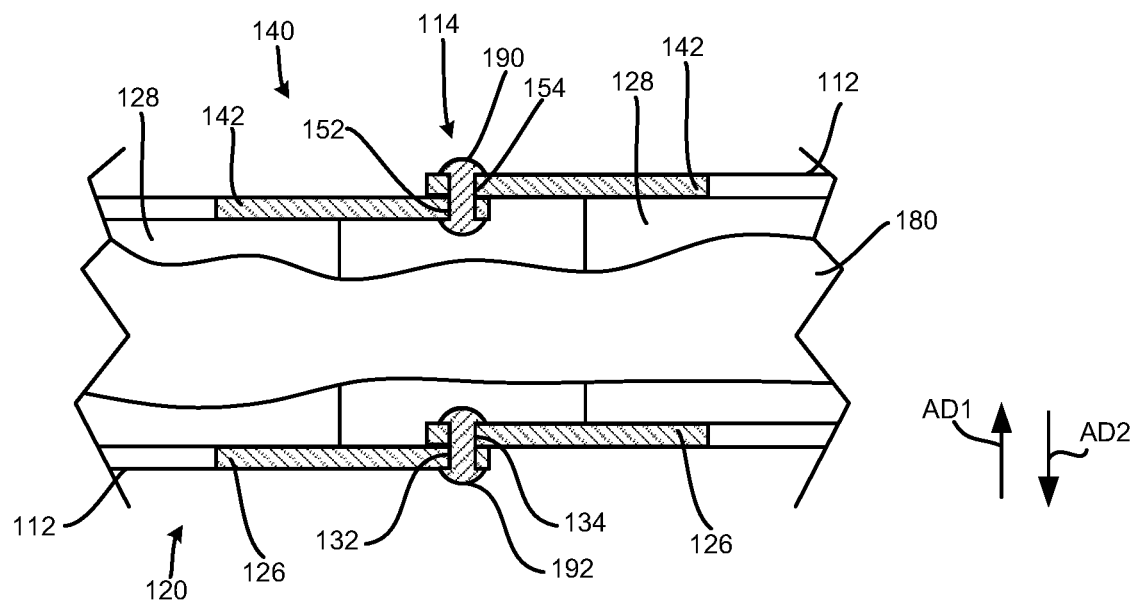
FIG. 12 is a cross-sectional view of the expandable intervertebral implant taken generally along line 12-12 in FIG. 7B.
Figure 13:
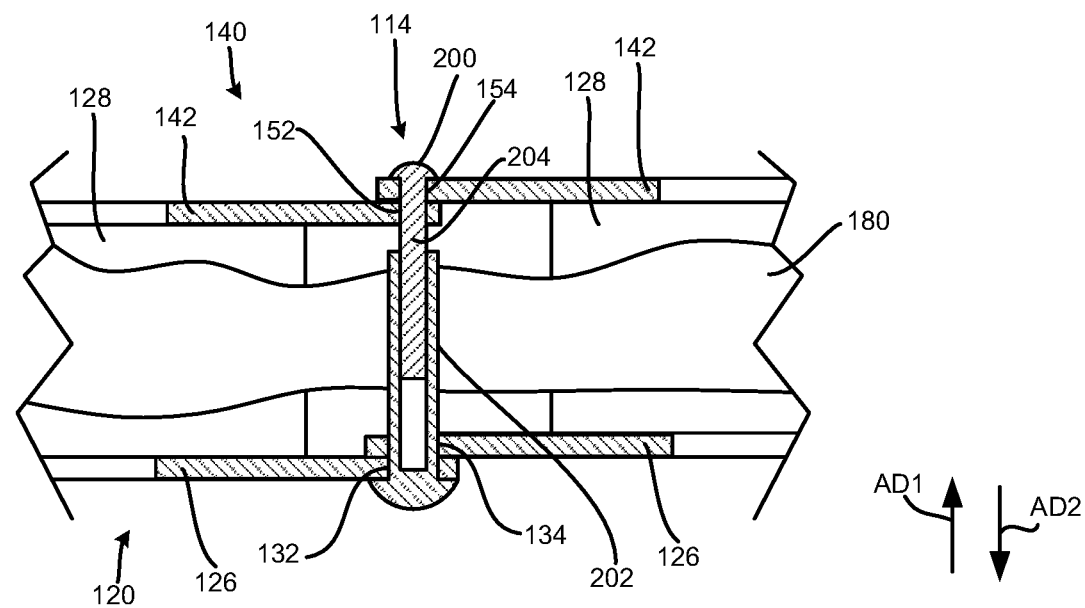
FIG. 13 is a cross-sectional view of the expandable intervertebral implant taken generally along line 13-13 in FIG. 7B.

FIG. 12 is a cross-sectional view of expandable intervertebral implant 110 taken generally along line 12-12 in FIG. 7B. FIG. 13 is a cross-sectional view of expandable intervertebral implant 110 taken generally along line 13-13 in FIG. 7B. FIGS. 12-13 show various embodiments of pivot connections between segments 12. As shown in FIG. 12, pivot 14 between segments 112 is embodied as connectors 190 and 192. Connectors 190 and 192 may comprise rivets, pins, bolts, screws, etc. Connector 190 extends through through-bores 154 and 152 to connect superior components 140 of adjacent segments 112 and connector 192 extends through through-bores 134 and 132 to connect inferior components 120 of adjacent segments 112.

As shown in FIG. 13, pivot 14 between segments 112 is embodied as connectors 190 and 192. Connectors 190 and 192 may comprise rivets, pins, bolts, screws, etc. Connector 200 extending through through-bores 154, 152, 134, and 132 to connect superior components 140 and inferior components 120 of adjacent segments. Specifically, connector 200 comprises sleeve portion 202 and pin portion 204, pin portion 204 and sleeve portion 202 being slidingly engaged. In some embodiment, sleeve portion 202 extends through through-bores 132 and 134, and pin portion 204 extends through through-holes 154 and 152. The advantages of connector 200 are that it connects superior components 140 and inferior components 120 of adjacent segments 112, and also connects superior component 140 and inferior component of each segment, thereby maintaining alignment thereof. Since pin portion 204 is displaceable in axial directions AD1 and AD2 with respect to sleeve portion 202, connector 200 does not hinder the expandability/collapsibility of implant 110.

Referring now to FIGS. 7A-C, implant 110 is operatively arranged to be implanted between adjacent vertebrae after the disc or a portion of the disc has been removed (i.e., in the disc space). As shown in FIG. 7A, implant 110 is arranged in a collapsed state so as to minimize the incision required for implantation into the disc space. For example, implant 110 is arranged in a linear array of segments with segments 112 arranged in two substantially straight lines next to each other. End 116 is arranged adjacent to end 118. Segments 112 are in a fully vertically collapsed state. Thus, the incision to insert implant 110 into the disc space need only be big enough to allow the front areas of implant 110 through (i.e., the height of segment 112 multiplied by the width of segment 112 multiplied by two). It should be appreciated that implant 110 can be arranged in any shape suitable for minimally invasive implantation.

Once arranged in the disc space, as shown in FIG. 7B, implant 110 is expanded in a later direction, namely, in radial direction RD1. In some embodiments, such radial expansion is generated using bladder or balloon 170. Bladder 170 is arranged along the radially inward facing surface of implant 110. Saline or another material that can be easily removed is injected into bladder 170 via port 170. As bladder 170 expands it engages protrusions 150 and/or protrusions 128 displacing segments 112 in radial direction RD1. Implant 110 will expand radially until segments 112 engage with surrounding tissue and/or until segments 112 are positioned adjacent the cortical ring of vertebrae. The shape of implant 110 in the desired laterally expanded state may comprise any suitable geometry, but in many cases will take the shape of the vertebral endplates. Advantageously, the pivotable connection of segments 112 allows implant 110 to take an infinite amount of geometric shapes. In some embodiments, the shape of implant 110 in the laterally expanded state forms a polygon (i.e., a closed polygonal chain or circuit). In some embodiments, the shape of implant 110 in the laterally expanded state is not a polygon (i.e., a non-closed plane figure).

Once implant 110 is laterally expanded to a desired shape/position, bladder 180 is inflated to vertically expand implant 110. As previously described, bladder 180 can be first filled with a removable material (e.g., saline) to obtain the required fill volume of bladder 180 that achieves the desired vertical expansion of implant 110, after which bladder 180 is filled with a hardenable material. In some embodiments (i.e., with respect to FIGS. 11A-B), bladder 180 is filled with a removable material to expand implant 110 to the desired height. Such expansion is maintained as the material is removed from bladder 180, for example, via engagement of teeth. Bladder 180 is then filled with a hardenable material. Alternatively, bladder 180 is removed and implant 110 is filled with bone material.

Once the material within implant 110 hardens, for example hardenable material within bladder 180 or bone material within segments 112, as shown in FIG. 7C bladder 170 is deflated and is removed from the disc space. As such, implant 110 in the desired laterally and vertically expanded state is left in situ. Bladder 170 may be removed from within implant 110 through lines 160 and 162 forming cavity C within implant 110 (i.e., formed by projections 130 and 150 of segments 112). In embodiments wherein ends 116 and 118 are directly connected, for example via pivot 114, deflated bladder 170 may be removed through a window in a segment 112. Cavity C is then filled with bone material to facilitate fusion of the adjacent vertebrae L3-4.

Figure 14:
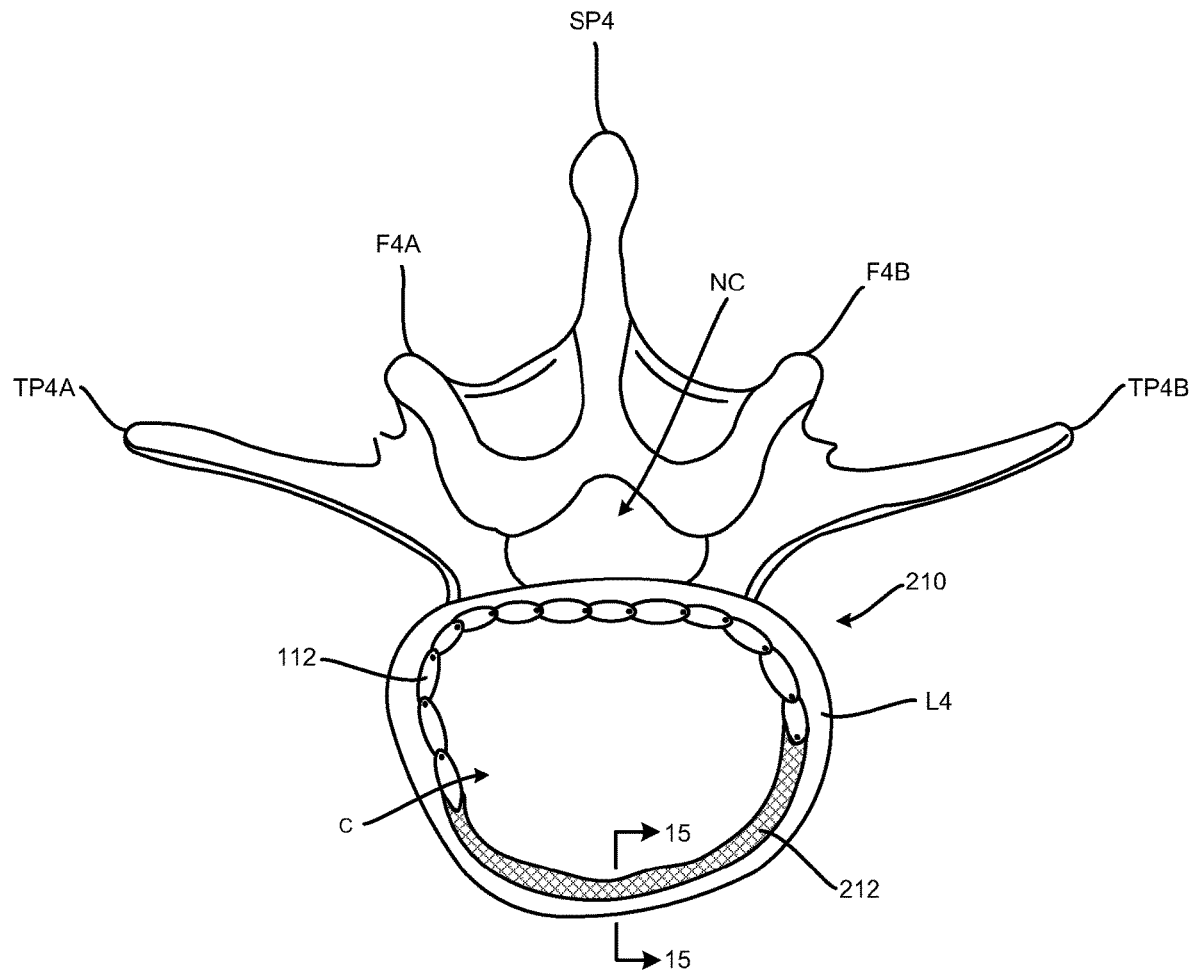
FIG. 14 is a top elevational view of an expandable intervertebral implant engaged with a vertebra in an expanded state; and, FIG. 15 is a cross-sectional view of the expandable intervertebral implant taken generally along line 15-15.
Figure 15:
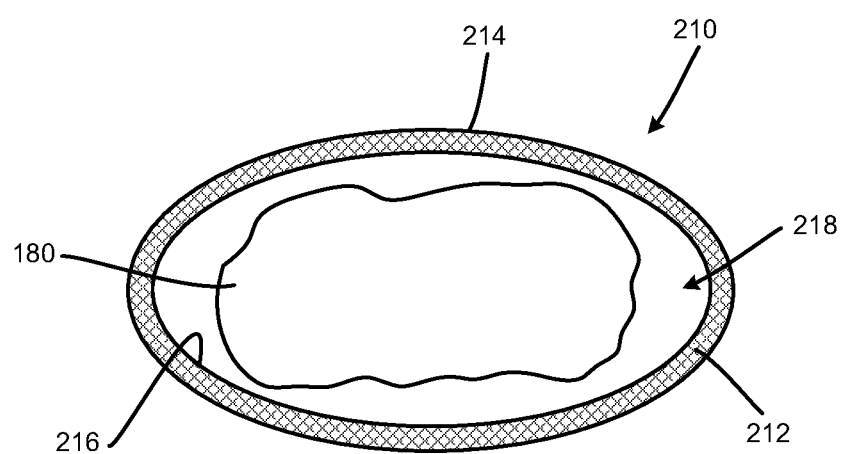

FIG. 14 is a top elevational view of expandable intervertebral implant 210 engaged with vertebra L4 in an expanded state. FIG. 15 is a cross-sectional view of expandable intervertebral implant 210 taken generally along line 15-15. As shown, in some embodiments, at least a portion of implant 210 comprises mesh tube 212, for example, a titanium mesh tube, including outer surface 214, and inner surface 216 forming internal cavity 218. Similar to segments 112 of implant 110, bladder 180 is arranged in internal cavity 218. As bladder 180 is injected with material, mesh tube 212 vertically expands to achieve the desired height. Also similar to implant 110, mesh tube 212 can be expanded laterally within the disc space via bladder 170 to form the desired shape (e.g., polygonal). In some embodiments, implant 210 comprises at least one segment 112 and at least one mesh tube 212 (see FIG. 14). For example, mesh tube 212 comprises a first end connected to a first end of the at least one segment 112 and a second end connected to a second end of the at least one segment 112. In some embodiments, implant 210 comprises just mesh tube 212 and no segments 112. In such embodiments, the ends of mesh tube 212 are connected essentially forming an expandable torus.

Thus it can be seen that the present disclosure has at least the following advantages: 1) implant 110, 210 requires only a minimal incision for insertion into a disc space since it can be shaped as a linear array; 2) once arranged in the disc space, implant 110, 210 can be laterally expanded to any geometric shape, and can thereby be used for any patent anatomy; 3) implant 110 can be vertically expanded; and, 4) implant 110, 210 is fillable with a large amount of bone material and therefore facilitates excellent bony fusion.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

A Annulus
C Coccyx
C1-C7 Cervical vertebrae
$D_{L1-L2}$ Disc
$D_{L2-L3}$ Disc
$D_{L3-L4}$ Disc
$D_{L4-L5}$ Disc
F Facet
FJ Facet joint
IF Intervertebral foramen
L1-L5 Lumbar vertebrae
N Nucleus
NC Neural canal
S Sacrum
SP Spinous process
TP Transverse process
T1-T12 Thoracic vertebrae
10 Spinal column
110 Expandable intervertebral fusion implant
112 Segment or module
114 Pivot or connector
116 End
118 End
120 Inferior component
122 Plate
124 Surface
126 Surface
128 Protrusion or wall
129 Tooth or teeth
130 Protrusion or wall
131 Tooth or teeth
132 Through-bore
134 Through-bore
136 Through-hole
140 Superior component
142 Plate
144 Surface
146 Surface
148 Protrusion or wall
149 Tooth or teeth
150 Protrusion or wall
151 Tooth or teeth
152 Through-bore
154 Through-bore
156 Through-hole
160 Line or connector or tether
162 Line or connector or tether
170 Bladder or balloon
172 Port
180 Bladder or balloon
182 Port
184 Port
190 Connector
192 Connector
200 Connector
202 Sleeve portion
204 Pin portion
210 Expandable intervertebral fusion implant
212 Sleeve
214 Outer surface
216 Inner surface
218 Internal cavity
AD1 Axial direction
AD2 Axial direction
C Cavity RD1 Radial direction
RD2 Radial direction

What is claimed is:

1. An expandable intervertebral fusion implant, comprising:
   a plurality of segments pivotably connected, each segment of the plurality of segments including:
      an inferior component; and
      a superior component engaged with the inferior component and forming a chamber therebetween; and
   a first expandable bladder arranged in the chamber of at least one segment and operatively arranged to displace the superior component with respect to the inferior component.

2. The expandable intervertebral fusion implant as recited in claim 1, wherein the plurality of segments form a first end and a second end, the second end being connected to the first end.

3. The expandable intervertebral fusion implant as recited in claim 1, wherein the plurality of segments are operatively arranged to form a polygon.

4. The expandable intervertebral fusion implant as recited in claim 1, wherein the plurality of segments form a radially inward facing surface, the first expandable bladder being arranged radially outward of the radially inward facing surface.

5. The expandable intervertebral fusion implant as recited in claim 4, further comprising a second expandable bladder engaged with the radially inward facing surface.

6. The expandable intervertebral fusion implant as recited in claim 5, wherein the second expandable bladder is operatively arranged to laterally expand the expandable intervertebral fusion implant.

7. The expandable intervertebral fusion implant as recited in claim 4, wherein the first expandable bladder is operatively arranged to vertically expand the expandable intervertebral fusion implant.

8. The expandable intervertebral fusion implant as recited in claim 1, wherein:
   the inferior component comprises a first plate arranged to engage a first vertebra and a first protrusion extending from the first plate; and
   the superior component comprises a second plate arranged to engage a second vertebra and a second protrusion extending from the second plate, the second protrusion engaged with the first protrusion.

9. The expandable intervertebral fusion implant as recited in claim 8, wherein the first plate, the second plate, and at least one of the first protrusion and the second protrusion form the chamber.

10. The expandable intervertebral fusion implant as recited in claim 8, wherein at least one of the first plate and the second plate comprises a through-hole.

11. The expandable intervertebral fusion implant as recited in claim 1, wherein the superior component engages the inferior component via a plurality of teeth.

12. The expandable intervertebral fusion implant as recited in claim 1, wherein the plurality of segments are pivotably connected via one or more pins.

13. The expandable intervertebral fusion implant as recited in claim 1, further comprising a mesh tube connected to at least one segment of the plurality of segments and including an internal cavity, the first expandable bladder arranged in the mesh tube.

14. An expandable intervertebral fusion implant, comprising:
   a plurality of segments pivotably connected, each segment of the plurality of segments including:
      an inferior component comprising a first plate and a first protrusion extending from the first plate;
      a superior component comprising a second plate and a second protrusion extending from the second plate, the second protrusion engaged with the first protrusion; and
      a chamber formed between the inferior component and the superior component; and
   a first expandable bladder arranged in the chamber of at least one segment;
   wherein:
      the superior component is displaceable with respect to the inferior component in a first direction; and
      the plurality of segments are displaceable in a second direction, different than the first direction.

15. The expandable intervertebral fusion implant as recited in claim 14, further comprising a radially inward facing surface formed by at least one of the first protrusion of the plurality of segments and the second protrusion of the plurality of segments.

16. The expandable intervertebral fusion implant as recited in claim 15, further comprising a second expandable bladder removably engaged with the radially inward facing surface.

17. The expandable intervertebral fusion implant as recited in claim 15, wherein the first expandable bladder is arranged radially outward of the first protrusion and the second protrusion.

18. The expandable intervertebral fusion implant as recited in claim 14, wherein the plurality of segments are capable of forming:
   a linear array of segments; and
   a polygon.

19. The expandable intervertebral fusion implant as recited in claim 14, wherein the first expandable bladder is operatively arranged to displace the superior component with respect to the inferior component.

20. An expandable intervertebral fusion implant, comprising:
   a plurality of segments pivotably connected, each segment of the plurality of segments including:
      an inferior component including a first plate and a first plurality of protrusions extending from the first plate;
      a superior component including a second plate and a second plurality of protrusions extending from the second plate, the second plurality of protrusions engaged with the first plurality of protrusions; and
      a chamber formed between the first plate and the second plate; and
   an expandable bladder arranged in the chamber of at least one segment and operatively arranged to displace the superior component with respect to the inferior component.

* * * * *